United States Patent
Bombardelli

(10) Patent No.: US 8,859,019 B2
(45) Date of Patent: *Oct. 14, 2014

(54) **COMPOSITIONS COMPRISING LIPOPHILIC EXTRACTS OF *ZINGIBER OFFICINALE* AND *ECHINACEA ANGUSTIFOLIA* FOR THE PREVENTION AND TREATMENT OF GASTRO-OESOPHAGEAL REFLUX AND CHEMOTHERAPY-INDUCED EMESIS**

(71) Applicant: Indena S.p.A., Milan (IT)

(72) Inventor: Ezio Bombardelli, Groppello Cairoli (IT)

(73) Assignee: Indena S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/721,298

(22) Filed: Dec. 20, 2012

(65) Prior Publication Data

US 2013/0108720 A1    May 2, 2013

Related U.S. Application Data

(62) Division of application No. 13/145,153, filed as application No. PCT/EP2010/000204 on Jan. 15, 2010, now Pat. No. 8,361,521.

(30) Foreign Application Priority Data

Jan. 20, 2009 (IT) .................. MI20090049

(51) Int. Cl.
 *A61K 36/28* (2006.01)
 *A61K 36/9068* (2006.01)

(52) U.S. Cl.
 CPC ............ *A61K 36/9068* (2013.01); *A61K 36/28* (2013.01)
 USPC .......................................... 424/737; 424/756

(58) Field of Classification Search
 CPC ......................... A61K 36/9068; A61K 36/28
 USPC .................................................. 424/756, 737
 See application file for complete search history.

(56) References Cited

U.S. PATENT DOCUMENTS

| | | | | |
|---|---|---|---|---|
| 6,261,607 | B1 * | 7/2001 | Newmark et al. | 424/727 |
| 6,274,177 | B1 * | 8/2001 | Wu et al. | 424/756 |
| 2008/0160116 | A1 | 7/2008 | Li et al. | |

FOREIGN PATENT DOCUMENTS

| | | | |
|---|---|---|---|
| DE | 198 59 499 A1 | 6/2000 | |
| EP | 0 464 298 A1 | 1/1992 | |
| WO | 99/21007 A1 | 4/1999 | |
| WO | 2008/070783 A2 | 6/2008 | |

* cited by examiner

*Primary Examiner* — Susan Hoffman
(74) *Attorney, Agent, or Firm* — Silvia Salvadori, P.C.

(57) ABSTRACT

The present invention relates to compositions consisting of a combination of lipophilic extracts of *Zingiber officinale* and *Echinacea angustifolia*, obtained by extraction with carbon dioxide under supercritical conditions, which are useful for the prevention and treatment of oesophageal reflux and chemotherapy-induced emesis.

4 Claims, No Drawings

COMPOSITIONS COMPRISING LIPOPHILIC EXTRACTS OF *ZINGIBER OFFICINALE* AND *ECHINACEA ANGUSTIFOLIA* FOR THE PREVENTION AND TREATMENT OF GASTRO-OESOPHAGEAL REFLUX AND CHEMOTHERAPY-INDUCED EMESIS

This application is a divisional of U.S. application Ser. No. 13/145,153 filed on Sep. 27, 2011, now U.S. Pat. No. 8,361,521, which is a 371 U.S. national phase of International Application No. PCT/EP2010/000204 filed on Jan. 15, 2010, which claims priority to and benefit of Italian Application No. MI2009000049 filed on Jan. 20, 2009, all of which are incorporated by reference herein in their entirety.

SUMMARY OF THE INVENTION

The present invention relates to compositions consisting of an association of lipophilic extracts of *Zingiber officinale* and *Echinacea angustifolia*, which are useful for the prevention and treatment of oesophageal reflux and chemotherapy-induced emesis.

PRIOR ART

Cancer of the gastrointestinal tract is the second most common form of cancer, and the second-highest cause of death when this area is affected. Oesophagus and stomach cancer are not very common in the industrialised countries, but are extremely lethal.

A number of contributory causes have been identified for these two tumours, such as abuse of spirits, often combined with smoking, a nitrate-rich diet, and/or products or habits that break the mucus barrier in the stomach and oesophagus. Following examination of eating habits and deficiencies of some trace elements in populations from different continents (Plummer-Vinson and Paterson-Kelly syndromes), attempts have been made to prevent the onset of carcinoma of the stomach and oesophagus due to said contributory causes by modifying eating habits and lifestyles, and using medicinal or diet products. Although many of said contributory causes have been eliminated, the global incidence has increased because of an increase in the number of people suffering from gastro-oesophageal reflux, often associated with diet and/or hiatus hernia, which is one of the main causes of oesophageal tumours. Adenocarcinoma is manifested by dysplastic columnar epithelium in the distal part of the oesophagus, nearly always in the presence of chronic reflux and gastric metaplasia of the epithelium (Barrett's oesophagus), which are common in obese individuals, and becomes malignant in over 50% of cases.

It is therefore very important to reduce the incidence of this disorder.

Research is consequently oriented towards drugs able to reduce reflux, especially by modifying gastric emptying. In particular, researchers are attempting to develop well-tolerated natural prokinetics, as the potential drug will have to be taken chronically for many years on a preventive basis, or discontinuously, depending on digestive requirements.

However, many drugs which have been used recently to modify gastric voiding present serious side effects affecting the CNS or have a carcinogenic action, and have therefore either been, or are about to be, withdrawn from the market. Gastro-oesophageal reflux is currently treated with a cocktail of drugs such as proton pump inhibitors (ranitidine, -prazoles or simple antacids), enzymes, various digestive drugs, and prokinetics such as domperidone. However, long-term use of proton pump inhibitors often leads to major digestive problems.

Research is consequently now oriented towards new therapeutic approaches.

DESCRIPTION OF THE INVENTION

It has now been found that a combination comprising lipophilic extracts of *Zingiber officinale* and *Echinacea angustifolia*, both prepared by extraction with carbon dioxide under supercritical conditions, has a surprising prokinetic and anti-emetic activity, leaving the digestive function unchanged and eliminating the feeling of heaviness of the stomach and nausea which are contributory causes of oesophageal reflux; it is therefore useful in the prevention and treatment of oesophageal reflux and chemotherapy-induced emesis.

The invention therefore relates to compositions containing:

a) a lipophilic extract of *Zingiber officinale*, and
b) a lipophilic extract of *Echinacea angustifolia*, for the prevention and treatment of oesophageal reflux and chemotherapy-induced emesis.

More specifically, according to the invention, the lipophilic extract of *Echinacea angustifolia* will be prepared by extraction with carbon dioxide under supercritical conditions as reported in patent EP 464298 filed by the applicant. The lipophilic extract of *Zingiber officinale* can also be extracted under the same conditions, starting with the pulverised roots.

The roots and rhizomes of ginger (*Zingiber officinale*), treated in various ways, are used, especially in Asia and the Middle East, as spices and in traditional medicine to treat indigestion, flatulence, diarrhoea, coughing, and, to a lesser extent, to protect the mucous membranes, against inflammation, to treat urinary incontinence, etc.

The active components present in the lipophilic extract of *Zingiber officinale* mainly consist of gingerols (generally present in concentrations ranging between 10 and 15%), which possess an anti-dyspeptic, anti-nausea and anti-vomiting activity, and are useful for the treatment of motion sickness, belching, indigestion, colic, vomiting, dyspepsia and stomach and colon pain. However, recent clinical trials have demonstrated that the lipophilic extract of *Zingiber officinale* prepared by traditional methods presents low activity in view of the well-known chemical instability of gingerols; the US pharmacopoeia therefore recommends a complete review of the properties attributed to the plant due to the lack of convincing evidence. The gingerols contained in the lipophilic extract of *Zingiber officinale* prepared by traditional methods break down rapidly, giving rise to a series of compounds, such as shogaol and other products of oxidation, which are devoid of efficacy. These conflicting data are partly due to the instability of the active components in the extracts normally used. However, the extract used in the present invention is a lipophilic extract, stabilised and prepared with carbon dioxide under well-defined supercritical conditions.

The lipophilic extract of the roots and aerial parts of *Echinacea angustifolia* is characterised by the presence of isobutylamides of polyunsaturated acids with analgesic and anti-inflammatory properties, anti-nausea and anti-vomiting activity, associated with their interaction with the cannabinoid receptors. The combination according to the invention possesses a surprisingly marked prokinetic and anti-dyspeptic effect, leaving the digestive function unchanged and eliminating the feeling of heaviness in the stomach and nausea which are contributory causes of oesophageal reflux. This combination can therefore be usefully employed in the prevention and treatment of oesophageal reflux and chemotherapy-induced emesis.

The compositions according to the invention increase gastric emptying, a highly potent and entirely unexpected effect, as said activity is not demonstrable for the individual components in any of the patients treated. Indeed, as stated above, it has been observed that the administration of alkylamides of *Echinacea angustifolia* slows gastric and intestinal voiding rather than promoting it.

According to a preferred aspect, the compositions according to the invention will contain the two components within the following weight intervals:
  a) lipophilic extract of *Zingiber officinale:* 1 to 25 mg; and
  b) lipophilic extract of *Echinacea angustifolia:* 1 to 10 mg.

According to a particularly preferred aspect, the compositions will contain the two components in the following quantities by weight:
  a) lipophilic extract of *Zingiber officinale:* 12.5 mg; and
  b) lipophilic extract of *Echinacea angustifolia:* 5 mg.

According to a preferred aspect, the compositions according to the invention will contain a lipophilic extract of *Echinacea angustifolia* prepared according to the process described in EP 464298, characterised by a 25-50% content in isobutylamides, in particular dodeca-2E,4E,8Z,10Z-tetraenoic acid isobutylamide.

According to a preferred aspect, the lipophilic extract of *Zingiber officinale* and the lipophilic extract of *Echinacea angustifolia* will be formulated in vegetable oils rich in 3/6 polyunsaturated fatty acids, such as evening primrose oil.

According to a further aspect, the compositions according to the invention may be administered together with other substances having a useful or complementary activity.

The doses which have proved active in man are 1 to 25 mg of lipophilic extract of *Zingiber officinale* and 1 to 10 mg of lipophilic extract of *Echinacea angustifolia* per dose; more particularly, 12.5 mg of lipophilic extract of *Zingiber officinale* and 5 mg of lipophilic extract of *Echinacea angustifolia* per dose, to be taken with every main meal or otherwise adapted to the disorder to be treated.

The compositions according to the invention will be formulated according to conventional methods, such as those described in "Remington's Pharmaceutical Handbook", Mack Publishing Co., N.Y., USA. In particular, the compositions according to the invention will be formulated according to conventional formulation techniques for lipophilic ingredients intended for oral administration, mainly as sublingual tablets or soft gelatin or cellulose capsules for oils designed to disperse rapidly in the stomach. The lipophilic form uses oils rich in –3 fatty acids, which promote rapid absorption of the active ingredient, to disperse the active components. Examples of oral formulations are tablets, dragées, soft and hard gelatin capsules, and cellulose capsules.

The following examples further illustrate the invention.

EXAMPLE 1

Soft Gelatin Capsules

Unit Composition:

| | |
|---|---|
| Lipophilic extract of *Zingiber officinale* | 12.5 mg |
| Lipophilic extract of *Echinacea angustifolia* | 5 mg |
| Soya lecithin | 10 mg |
| Evening primrose oil | 150 mg |

EXAMPLE 2

Hard Gelatin Capsules

Unit Composition:

| | |
|---|---|
| Lipophilic extract of *Zingiber officinale* | 12.5 mg |
| Lipophilic extract of *Echinacea angustifolia* | 5 mg |
| Soya lecithin | 10 mg |
| Microcrystalline cellulose | 200 mg |
| Maize starch | 50 mg |
| Magnesium stearate | 2 mg |
| Silicon dioxide | 2 mg |

The invention claimed is:

1. A composition consisting essentially of two components:
  a) lipophilic extract of *Zingiber officinale*; and
  b) lipophilic extract of *Echinacea angustifolia*,
  obtained by extraction with carbon dioxide under supercritical conditions,
  wherein the two components are in the following amounts by weight:
  a) lipophilic extract of *Zingiber officinale:* 12.5 mg; and
  b) lipophilic extract of *Echinacea angustifolia:* 5 mg.

2. The composition according to claim 1, wherein the lipophilic extract of *Echinacea angustifolia* has a 25 to 50% content of isobutylamides.

3. The composition according to claim 1, for oral administration.

4. The composition as claimed in claim 3 in the form of soft gelatin capsules or hard gelatin capsules.

\* \* \* \* \*